[19] United States Patent
Lash et al.

[11] 4,366,036
[45] Dec. 28, 1982

[54] ADDITIVE AND ALKALINE ZINC ELECTROPLATING BATH AND PROCESS USING SAME

[75] Inventors: Ronald J. Lash, Rochester; Roy W. Herr, Troy, both of Mich.

[73] Assignee: Occidental Chemical Corporation, Warren, Mich.

[21] Appl. No.: 300,316

[22] Filed: Sep. 8, 1981

[51] Int. Cl.³ .................. C25D 3/22; C07D 231/06; C07C 95/08; C07D 233/04
[52] U.S. Cl. ........................ 204/55 R; 204/55 Y; 542/455; 548/341; 560/38; 560/39; 564/285; 564/287; 564/288; 564/292
[58] Field of Search ............ 542/455; 548/341; 560/38, 39; 564/285, 287, 288, 292; 204/55 R, 55 Y, 43 Z, 114, 123

[56] References Cited

U.S. PATENT DOCUMENTS

| 3,629,461 | 12/1971 | Payot | 564/287 X |
| 3,801,641 | 4/1974 | Payot et al. | 564/285 X |
| 4,113,583 | 9/1978 | Oshima et al. | 204/55 Y |

FOREIGN PATENT DOCUMENTS

| 236587 | 11/1959 | Australia | 564/285 |
| 259790 | 2/1963 | Australia | 564/287 |
| 7005765 | 10/1970 | Netherlands | 564/287 |
| 502301 | 3/1971 | Switzerland | 564/287 |
| 935613 | 8/1963 | United Kingdom | 564/287 |

Primary Examiner—G. L. Kaplan
Attorney, Agent, or Firm—Richard P. Mueller

[57] ABSTRACT

Novel alkylated hydroxyl aryl compounds, such as vanillin which has been alkylated with 3-chloro-2-hydroxypropyltrimethylammonium chloride, are useful as additives in alkaline zinc electroplating baths.

17 Claims, No Drawings

ADDITIVE AND ALKALINE ZINC ELECTROPLATING BATH AND PROCESS USING SAME

BACKGROUND OF THE INVENTION

The present invention relates to an alkaline zinc electroplating bath and process and to novel organic compounds useful as additives therein. The novel compound of this invention is an alkylated hydroxyl aryl compound which can be advantageously employed for a brightening and/or stain preventing effect in cyanide-containing or cyanide-free alkaline zinc electroplating baths.

Alkaline zinc electroplating is conventionally carried out in alkaline baths which contain cyanide, which has a beneficial effect in achieving a bright, uniform zinc plate over a wide range of current densities. However, the increasing expense of using cyanide containing baths with the attendent waste disposal problems has lead to the development of cyanide-free plating baths. One technique for cyanide-free alkaline zinc electroplating involves use of a plating bath comprising sodium zincate electrolyte. Unfortunately, cyanide-free baths are commonly sensitive to build-up of both metallic and organic contaminants in the plating system. While the bath may initially perform well, it is subject to deteriorating performance as increasingly dark deposits may be encountered upon subsequent bright dipping passivation steps.

In accordance with the present invention, a novel compound has been discovered which is broadly useful as an additive in alkaline zinc electroplating baths. Thus, the novel compound of the present invention is useful as a brightener and anti-staining additive to cyanide-containing alkaline zinc electroplating baths and is particularly useful as a brightener and anti-staining additive to alkaline zinc plating baths which are cyanide-free such as sodium zincate baths. The plating baths of this invention are suitable for zinc plating over a wide current density range and are useful with all types of conversion coatings including chromate and non-chromate conversion coatings.

Further understanding of the present invention will be had from the following disclosure wherein all parts and percentages are by weight unless specifically indicated otherwise.

SUMMARY OF THE INVENTION

The present invention relates to novel compounds, zinc electroplating baths comprising the compounds and electroplating processes using the compounds. The novel compounds of the present invention are alkylated hydroxyl aryl compounds, for example, vanillin which has been alkylated with 3-chloro-2 hydroxypropyltrimethylammonium chloride. The novel compounds have been found to be useful as additives in alkaline zinc electroplating baths, for example, as a brightener and/or an anti-staining additive over a wide current density range. An alkaline zinc electroplating bath of the present invention comprises the novel additive compound. The method of the present invention comprises electrodepositing a zinc deposit from the bath of the present invention onto a substrate surface.

DESCRIPTION OF THE PREFERRED EMBODIMENTS

The novel compounds of the present invention have the following structural formula:

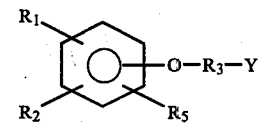

wherein $R_1$ is selected from the group consisting of hydrogen, alkyl having 1–4 carbon atoms, and alkoxy having from 1–4 carbon atoms;

$R_2$ is selected from the group consisting of an aldehyde moiety and a bisulfite adduct of an aldehyde moiety;

$R_3$ is selected from the group consisting of alkyl having from 1–6 carbon atoms, hydroxy alkyl having from 2–6 carbon atoms, alkenyl having from 2–6 carbon atoms, alkynyl having from 2–6 carbon atoms, hydroxy alkenyl having from 3–6 carbon atoms, hydroxy alkynyl having from 3–6 carbon atoms, oxo alkyl having from 2–6 carbon atoms, and oxo alkenyl having from 3–6 carbon atoms;

Y is selected from the group consisting of:

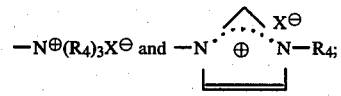

X is a halogen or sulfate;

$R_4$ is selected from the group consisting of alkyl, hydroxy alkyl, and carboxy alkyl, each alkyl having from 1–4 carbon atoms; and $R_5$ is hydrogen or another adjoining fused six membered aromatic ring.

Compounds of the invention can be made, for example, by alkylating a hydroxy aryl compound such as vanillin with a trialkyl ammonio-halo-alkyl halide salt such as 3-chloro-2 hydroxypropyltrimethylammonium chloride using conventional techniques. Further understanding of the compounds and their making can be had from the specific Examples I–III.

Specific and preferred compounds of the present invention are:

the compound of Example I, 3-(4-formylphenoxy)-2-hydroxypropyltrimethylammonium chloride;

the compound of Example II, 3-(4-formyl-2-methoxyphenoxy)-2-hydroxypropyltrimethylammonium chloride; and the compound of Example III, 3-(3-(4-formyl-2-methoxyphenoxy)-2-hydroxypropyl)-1-methylimidazolium chloride, bisulfite adduct.

The compounds of this invention are useful as additives to alkaline zinc electroplating baths generally and can be advantageously employed in cyanide-free, alkaline zinc electroplating baths. The additives are useful, for example, as a brightener and to prevent or reduce the development, upon subsequent bright dipping passivation steps, of dark staining on a zinc plate deposited from a cyanide-free alkaline zinc bath comprising the additive. In addition, the additives provide a brightening effect in a cyanide containing bath and can be used as an anti-staining additive therein should staining from copper or other metal ions occur. The additives are effective over a broad current density range.

The additives of this invention are employed in the working bath in a concentration effective to obtain the additive effect desired, such as an anti-staining effect or a brightening effect. Generally, the additives are employed in a concentration within the range of from about 0.1 g/l to about 10 g/l, and preferably from about 0.5 g/l to about 5 g/l.

In addition to the additive compound, a plating bath of this invention comprises zinc ion or zincate ion for deposition of zinc metal therefrom. The source of zinc in the bath can be provided in a conventional manner. For example, prepared concentrated solutions of zincate ion are commercially available. Alternatively, zincate ion can be obtained by dissolving high purity zinc metal in enough high purity sodium hydroxide to complex the zinc. It will, of course, be appreciated that zinc or zincate ion is employed herein in an amount effective to electrodeposit zinc up to an amount which no longer gives satisfactory electrodeposits. Typically, concentrations of from about 2 to about 30 g/l, preferably from about 4 to about 15 g/l (based on zinc metal) are employed in the working bath. Typical concentrations of sodium hydroxide are from about 50 to about 90 g/l and typical concentrations of sodium cyanide are from about 8 to about 112 g/l.

The working bath or solution may also comprise one or more additional brighteners. In particular, the compound of this invention enhances brightness and luster of the zinc deposit when used in conjunction with a brightener selected from the group consisting of polyvinyl alcohol, polyethylene polyamines or quaternary salts thereof, quaternized pyridine carboxylic acids, condensation polymers of an epichlorohydrin and a heterocyclic compound of at least two nitrogen atoms, and mixtures thereof.

Of course, other optional ingredients of the type conventionally employed in alkaline zinc electroplating baths may also be employed in the working bath of this invention. Thus, grain refiners, wetting agents, buffering agents, complexing agents, and the like may be used herein.

In use, the bath of the present invention not only provides a bright zinc deposit with good grain refinement but also is tolerant to extended use and to the presence of contaminating metal ions, such as ferric ions, in the bath.

Electroplating of zinc from a bath of the present invention can be conducted in a conventional manner. Plating can be carried out at cathode current densities of from about 5 to about 80 amps per sq. ft. with or without agitation. The bath is normally employed at room temperature although temperatures up to 55° C. may be used. Preferably, the bath or solution is used at from about 20° to about 35° C. Further understanding of the present invention will be obtained from the following Examples.

EXAMPLE I

A novel compound of the present invention is made by the following procedure:

p-hydroxybenzaldehyde (15.9 g, 0.13 mole) and water (50 ml) are mixed and then sodium hydroxide (6.8 ml, 50%, 0.13 mole) is added when mixing. The mixture is then heated to 85° C. and 3-chloro-2-hydroxypropyltrimethylammonium chloride (50% aqueous solution of 24 g (0.13 mole) is added slowly for 3 hours. The reaction product is a compound of the structural formula:

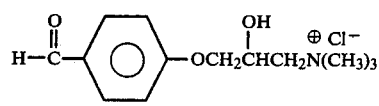

3-(4-formylphenoxy)-2-hydroxypropyltrimethylammonium chloride.

EXAMPLE II

Vanillin (10 g, 0.065 mole, in 25 ml water) and an equimolar quantity of sodium hydroxide are mixed together and a solution of 3-chloro-2-hydroxypropyltrimethylammonium chloride (50% aqueous solution of 24.7 g, 0.065 mole) is added slowly. The mixture is refluxed for 1½ hours. The reaction product is a compound of the structural formula:

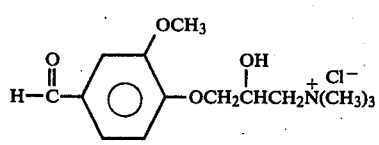

3(4-formyl-2-methoxyphenoxy)-2-hydroxypropyltrimethylammonium chloride.

EXAMPLE III

One equivalent of hydrochloric acid (52 ml, 0.628 mole) is added to 1-methyl imidazole (50 ml, 0.628 mole) and then an equimolar amount of epichlorohydrin (68.5 ml, 0.628 mole) is dripped in slowly. The mixture is refluxed 5 hours and then added to a solution of vanillin sodium salt (95.45 g, 0.628 mole vanillan, 32.8 ml 50% NaOH and 100 ml H$_2$O), refluxed 3 hours and then cooled giving a yellow solid which was reacted (40 g, 0.122 mole, 100 ml H$_2$O) with sodium bisulfite (12.4 g, 0.130 mole) to increase water solubility. The reaction product is a compound having the structural formula:

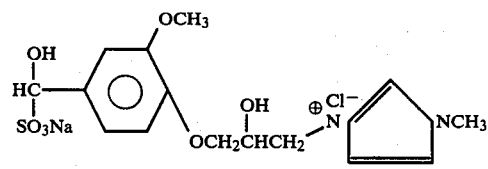

3-(3-(4-formyl-2-methoxyphenoxy)-2-hydroxypropyl)-1-methylimidazolium chloride, bisulfite adduct.

EXAMPLE IV

A zinc plating bath is prepared according to the following formulation:

| | |
|---|---|
| Zinc Metal | 7.8 g/l |
| Sodium Hydroxide | 83 g/l |
| 3-(4-formyl-2-methoxyphenoxy)-2-hydroxypropyltrimethylammonium chloride | 1 g/l |

A polished steel panel is cleaned and plated in a 267 ml Hull Cell at 2 amperes cell current for 10 minutes at a temperature of 28° C. without solution agitation. The zinc plate is bright below 30 A/ft² with a clear conversion coating passivate produced upon post treatment.

EXAMPLE V

A zinc plate is electrodeposited following the procedure of Example IV from a bath prepared according to the following formulation:

| | |
|---|---|
| Zinc Metal | 9 g/l |
| Sodium Hydroxide | 90 g/l |
| 3-(3-(4-formyl-2-methoxyphenoxy)-2-hydroxy propyl)-1-methylimidazolium chloride, bisulfite adduct | 0.9 g/l |

The zinc plate is bright below 30 ASF and has good grain refinement up to 50 ASF with a clear conversion coating passivate produced upon post treatment.

EXAMPLE VI

A zinc plate is electrodeposited as in Example IV from a bath prepared according to the following formulation:

| | |
|---|---|
| Zinc Metal | 6 g/l |
| Sodium Hydroxide | 70 g/l |
| Ferric Ion | 0.0075 g/l |
| Polyethylene imine (MW 1000) reaction product with 3-chloro-2-hydroxypropyltrimethylammonium chloride (In accordance with U.S. Pat. No. 3,853,718, Dec. 10, 1974, to Creutz) | 0.5 g/l |

The zinc plate is bright to semi-bright between 1–40 A/ft², and semi-bright to 80 A/ft². Upon immersion in a blue-bright conversion coating bath the zinc plate turns non-uniformly discolored with dark brown stains and blemishes without specificity to current density.

To the bath is then added 0.5 g/l of 3-(4-formyl-2-methoxyphenoxy)-2-hydroxypropyltrimethylammonium chloride and a zinc plate is again electrodeposited from the bath following the procedure of Example IV. The zinc deposit is bright and uniformly clear from dark staining after a chromate conversion coating step.

EXAMPLE VII

A zinc electroplating bath is prepared according to the following formulation:

| | |
|---|---|
| Zinc Metal | 35 g/l |
| Sodium hydroxide | 81 g/l |
| Sodium Cyanide | 88 g/l |

A polished steel test panel is cleaned and plated in a 267 ml Hull Cell at 1 ampere for 5 minutes at a temperature of 26° C. without solution agitation. The resulting deposit is dull to semibright and lacks uniform appearance.

To the above bath is added the following:

| | |
|---|---|
| 3-(4-formyl-2-methoxy-phenoxy)-2-hydroxy propyl-trimethylammonium chloride | 1.0 g/l |

A second panel is plated following the above procedures. The resulting zinc deposit is fully bright and suitable for industrial or decorative application in the current density region from 1 to 40 A/ft².

What is claimed is:

1. A compound having the following structural formula:

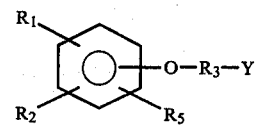

wherein
$R_1$ is selected from the group consisting of hydrogen, alkyl having 1–4 carbon atoms, and alkoxy having from 1–4 carbon atoms;
$R_2$ is selected from the group consisting of an aldehyde moiety and a bisulfite adduct of an aldehyde moiety;
$R_3$ is selected from the group consisting of alkyl having from 1–6 carbon atoms, hydroxy alkyl having from 2–6 carbon atoms, alkenyl having from 2–6 carbon atoms, alkynyl having from 2–6 carbon atoms, hydroxy alkenyl having from 2–6 carbon atoms, hydroxy alkynyl having from 3–6 carbon atoms, keto alkyl having from 2–6 carbon atoms, and keto alkenyl having from 3–6 carbon atoms;
Y is selected from the group consisting of

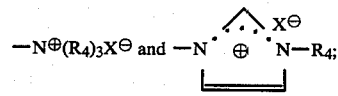

X is a halogen or sulfate;
$R_4$ is selected from the group consisting of alkyl hydroxy alkyl, and carboxy alkyl, each alkyl having from 1–4 carbon atoms; and
$R_5$ is hydrogen or another adjoining fused six membered aromatic ring.

2. A compound as in claim 1, said compound being 3-(4-formylphenoxy)-2-hydroxypropyltrimethylammonium chloride.

3. A compound as in claim 1, said compound being 3-(4-formyl-2-methoxyphenoxy)-2-hydroxypropyltrimethylammonium chloride.

4. A compound as in claim 1, said compound being 3-(3-(4-formyl-2-methoxyphenoxy)-2-hydroxypropyl)-1-methylimidazolium chloride, bisulfite adduct.

5. An alkaline zinc electroplating bath comprising an effective amount of a compound having the following structural formula:

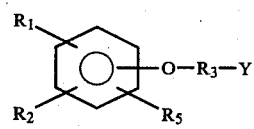

wherein
$R_1$ is selected from the group consisting of hydrogen, alkyl having 1–4 carbon atoms, and alkoxy having from 1–4 carbon atoms;
$R_2$ is selected from the group consisting of an aldehyde moiety and a bisulfite adduct of an aldehyde moiety;

R₃ is selected from the group consisting of alkyl having from 1-6 carbon atoms, hydroxy alkyl having from 2-6 carbon atoms, alkenyl having from 2-6 carbon atoms, alkynyl having from 2-6 carbon atoms, hydroxy alkenyl having from 2-6 carbon atoms, hydroxy alkynyl having from 3-6 carbon atoms, keto alkyl having from 2-6 carbon atoms, and keto alkenyl having from 3-6 carbon atoms;

Y is selected from the group consisting of

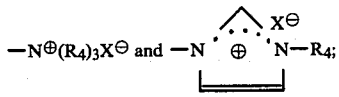

X is a halogen or sulfate;

R₄ is selected from the group consisting of alkyl hydroxy alkyl, and carboxy alkyl, each alkyl having from 1-4 carbon atoms; and R₅ is hydrogen or another adjoining fused six membered aromatic ring.

6. A bath as in claim 5 wherein said compound is 3-(4-formylphenoxy)-2-hydroxypropyltrimethylammonium chloride.

7. A bath as in claim 6 comprising zincate ion in an amount effective to electrodeposit zinc therefrom.

8. A bath as in claim 7 wherein said compound is present in a concentration of from about 0.1 g/l to about 10 g/l.

9. A bath as in claim 5 wherein said compound is 3-(4-formyl-2-methoxyphenoxy)-2-hydroxypropyltrimethylammonium chloride.

10. A bath as in claim 9 comprising zincate ion in an amount effective to electrodeposit zinc therefrom.

11. A bath as in claim 10 wherein said compound is present in a concentration of from about 0.1 g/l to about 10 g/l.

12. A bath as in claim 5 wherein said compound is 3-(3-(4-formyl-2-methoxyphenoxy)-2-hydroxypropyl)-1-methylimidazolium chloride, bisulfite adduct.

13. A bath as in claim 8 comprising zincate ion in an amount effective to electrodeposit zinc therefrom.

14. A bath as in claim 13 wherein said compound is present in a concentration of from about 0.1 g/l to about 10 g/l.

15. A bath as in claim 5 comprising zincate ion in an amount effective to electrodeposit zinc therefrom.

16. A bath as in claim 15 wherein said zincate ion is present in a concentration of from about 2 g/l to about 30 g/l based on zinc metal.

17. The process comprising electrodepositing zinc onto a substrate from a bath of anyone of claims 5-14.

* * * * *